United States Patent
Moinet et al.

(10) Patent No.: US 8,362,057 B2
(45) Date of Patent: Jan. 29, 2013

(54) IMIDAZOLECARBOXAMIDE DERIVATIVES AS FRUCTOSE-1,6-BISPHOSPHATASE INHIBITORS, AND PHARMACEUTICAL COMPOSITIONS COMPRISING SAME

(75) Inventors: Gérard Moinet, Orsay (FR); Gérard Botton, Buc (FR); Annick Arbellot de Vacqueur, Fontenay les briis (FR)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 1397 days.

(21) Appl. No.: 11/997,514

(22) PCT Filed: Jul. 7, 2006

(86) PCT No.: PCT/EP2006/006643
§ 371 (c)(1),
(2), (4) Date: Jan. 31, 2008

(87) PCT Pub. No.: WO2007/014619
PCT Pub. Date: Feb. 8, 2007

(65) Prior Publication Data
US 2008/0207720 A1   Aug. 28, 2008

(30) Foreign Application Priority Data
Aug. 1, 2005   (FR) ...................... 05 08211

(51) Int. Cl.
*A61K 31/4172* (2006.01)
*A61K 31/4178* (2006.01)
*C07D 233/88* (2006.01)

(52) U.S. Cl. ..................... 514/397; 548/315.4

(58) Field of Classification Search ............... 548/311.1; 514/397
See application file for complete search history.

(56) References Cited

U.S. PATENT DOCUMENTS

| | | |
|---|---|---|
| 5,658,889 A | 8/1997 | Gruber et al. |
| 2003/0114505 A1 | 6/2003 | Ueno et al. |
| 2008/0207720 A1 | 8/2008 | Moinet et al. |

FOREIGN PATENT DOCUMENTS

| | | |
|---|---|---|
| EP | 1 258 484 A1 | 11/2002 |
| JP | 11-147823 | * 6/1999 |
| WO | WO 97/31900 A | 9/1997 |
| WO | WO 2007/014619 A1 | 2/2007 |

OTHER PUBLICATIONS

Copending U.S. Appl. No. 12/681,380, commonly assigned to Merck.*
Machine translation of JP 11-147823. Obtained from <http://dossier.ipdl.inpit.go.jp/text_trans.html> Accessed May 2, 2012.*
Voet, A. B. et al: <<Prebiotic adenine synthesis from hydrocyanic acid—evidence for a newly discovered major pathway>> Bioorganic Chemistry, 12 (1), 8-17 CODEN : BOCMBM; ISSN: 0145-2068, 1983, XP009065660 compound 4.
Shaw G et al: "Purined, pyrimidines, and glyoxalines. XIII. New unambiguous synthesis of 5-amino-glyoxalines and 5-aminoglyoxaline-4-carboxamides, and a synthesis of 5-amino-1-beta..-D-ribofuranosylglyoxaline-4-carboxamide" Journal of The Chemical Society, Chemical Society. Letchworth, GB, 1959, pp. 1648-1655, XP009065659 ISSN: 0368-1769 Compound on p. 1653 lines 6-7.
International Search Report of PCT/EP2008/007367 (Jan. 7, 2009).

* cited by examiner

*Primary Examiner* — Joseph K. McKane
*Assistant Examiner* — Alicia L Otton
(74) *Attorney, Agent, or Firm* — Millen, White, Zelano & Branigan, P.C.

(57) ABSTRACT

The invention relates to the compounds of the general formula (I):

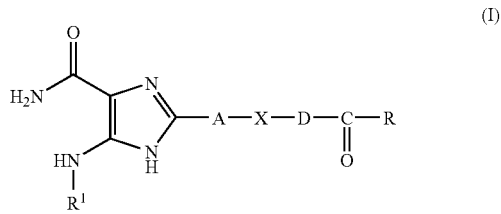

in which A, D, R, $R^1$ and X are as defined in the description, to a process for the preparation thereof and to the therapeutic use thereof in the treatment of pathologies associated with insulin resistance syndrome.

6 Claims, No Drawings

IMIDAZOLECARBOXAMIDE DERIVATIVES AS FRUCTOSE-1,6-BISPHOSPHATASE INHIBITORS, AND PHARMACEUTICAL COMPOSITIONS COMPRISING SAME

FIELD OF THE INVENTION

The present invention relates to imidazolecarboxamide derivatives that are inhibitors of fructose-1,6-bisphosphatase, to the preparation thereof and to the therapeutic use thereof in the treatment of pathologies associated with insulin resistance syndrome.

TECHNICAL BACKGROUND

"Diabetes mellitus" (or diabetes) is one of the most prevalent diseases in the world today. Individuals suffering from diabetes have been divided into two classes, namely type I or insulin-dependent diabetes mellitus and type II or non-insulin-dependent diabetes mellitus (NIDDM). Non-insulin-dependent diabetes mellitus (NIDDM) accounts for approximately 90% of all diabetics, and is estimated to affect 12 to 14 million adults in the United States alone (6.6% of the population).

NIDDM is characterized both by fasting hyperglycaemia and exaggerated postprandial increases in plasmatic glucose levels. NIDDM is associated with a variety of long-term complications, including microvascular diseases, such as retinopathy, nephropathy and neuropathy, and macrovascular diseases, such as coronary heart disease.

Numerous studies in animal models show a causal relationship between long-term complications and hyperglycaemia. Recent results obtained by the Diabetes Control and Complications Trial (DCCT) and the Stockholm Prospective Study have for the first time demonstrated this relationship in man by showing that insulin-dependent diabetics have a substantially lower risk of development and progression of these complications if they are subjected to tighter glycaemic control. Tighter control is also expected to benefit NIDDM patients.

Current therapies used for the treatment of NIDDM patients involve both controlling lifestyle risk factors and pharmaceutical intervention. First-line therapy for NIDDM patients is usually a strictly controlled regimen of diet and exercise, since an overwhelming number of NIDDM patients are overweight or obese ($\approx$67%) and since loss of weight can improve insulin secretion and insulin sensitivity, and lead to normoglycaemia.

Normalization of blood glucose takes place in fewer than 30% of these patients due to poor compliance and poor response. Patients suffering from hyperglycaemia not controlled by diet alone are subsequently treated with insulin or oral hypoglycaemiants. At the present time, insulin secretors (sulfonylureas and glinides), biguanides (metformin) and insulin sensitizers (glitazone) are the only classes of oral hypoglycaemiants available for NIDDM. Treatment with sulfonylureas leads to an effective reduction in blood glucose in only 70% of patients and only 40% after 10 years of therapy. Patients for whom diet and sulfonylureas have no effect are then treated with daily insulin injections in order to establish adequate glycaemic control.

Although sulfonylureas represent a major therapy for NIDDM patients, four factors limit their overall success. Firstly, as indicated above, a large proportion of the NIDDM population does not respond adequately to sulfonylurea therapy (i.e. primary failures) or becomes resistant (i.e. secondary failures). This is particularly true in the case of NIDDM patients with advanced NIDDM, due to the fact that these patients suffer from severely impaired insulin secretion. Secondly, sulfonylurea therapy is associated with an increased risk of severe hypoglycemic episodes. Thirdly, chronic hyperinsulinemia is associated with an increase in cardiovascular diseases, although this relationship is considered controversial and unproven. Finally, sulfonylureas are associated with weight gain, which leads to worsening of peripheral insulin sensitivity and may consequently accelerate the progression of the disease.

Recent results from the UK Diabetes Prospective Study also show that patients subjected to maximal therapy of a sulfonylurea, metformin, or a combination of the two, were unable to maintain normal fasting glycaemia over the six-year period of the UK Prospective Diabetes Study, 16. *Diabetes*, 44, 1249-158 (1995). These results also illustrate the great need for alternative therapies. Three therapeutic strategies that could provide additional benefits as regards the health of NIDDM patients beyond the currently available therapies include medicaments that would: (i) prevent the onset of NIDDM; (ii) prevent diabetic complications by blocking harmful events precipitated by chronic hyperglycaemia; or (iii) normalize glucose levels or at least reduce glucose levels below the threshold reported for microvascular and macrovascular diseases.

Hyperglycaemia in the case of NIDDM sufferers is associated with two biochemical abnormalities, namely insulin resistance and impaired insulin secretion. The relative roles of these metabolic abnormalities in the pathogenesis of NIDDMs have been the subject of numerous studies over the last several decades. Studies performed on the offspring and siblings of NIDDM patients, on monozygotic and dizygotic twins, and on ethnic populations with a high incidence of NIDDM (for example Pima Indians), strongly support the hereditary nature of the disease.

Despite the presence of insulin resistance and impaired insulin secretion, fasted blood glucose (FBG) levels remain normal in the case of pre-diabetic patients on account of a state of compensatory hyperinsulinemia. Eventually, however, the insulin secretion is inadequate and leads to fasting hyperglycaemia. Over time, the insulin levels decrease. Progression of the disease is characterized by increasing FBG levels and decreasing insulin levels.

Numerous clinical studies have attempted to define the primary defect involved during the progressive increase in FBG levels. The results of these studies show that excessive hepatic glucose output (HGO) is the first reason for the increase in the FBG levels, with a significant correlation found for HGO and FBG once the FBG levels exceed 140 mg/dL. Kolterman et al., *J. Clin. Invest.*, 68, 957, (1981); DeFronzo, *Diabetes*, 37, 667, (1988).

HGO comprises glucose derived from the breakdown of hepatic glycogen (glycogenolysis) and glucose synthesized from 3-carbon precursors (gluconeogenesis). A large number of radioisotopic studies, and also several studies using $^{13}$C-NMR spectroscopy, show that gluconeogenesis accounts for 50% to 100% of the glucose produced by the liver in the post-absorptive state and that the gluconeogenesis flux is excessive (2- to 3-fold) in the case of NIDDM patients. Magnusson et al., *J. Clin. Invest*, 90, 1323-1327, (1992); Rothmann et al., *Science*, 254, 573-76, (1991); Consoli et al., *Diabetes*, 38, 550-557, (1989).

Gluconeogenesis from pyruvate is a highly regulated biosynthetic pathway that requires eleven enzymes. Seven enzymes catalyse reversible reactions and are common to both gluconeogenesis and glycolysis. Four enzymes catalyse reactions specific to gluconeogenesis, namely pyruvate carboxylase, phosphoenolpyruvate carboxykinase, fructose-1,6-bisphosphatase and glucose-6-phosphatase. Overall flux is controlled throughout the biosynthetic pathway by the specific activities of these enzymes, the enzymes that catalyse the corresponding steps in the glycolytic direction, and by substrate availability. Dietary factors (glucose, fat) and hormones (insulin, glucagon, glucocorticoids, epinephrine) co-ordinatively regulate the enzymatic activities in the gluconeogenesis and glycolysis processes by means of gene expression and post-translational mechanisms.

Among the four enzymes specific to gluconeogenesis, fructose-1,6-bisphosphatase (referred to hereinbelow as "FBPase") is a very suitable target for a gluconeogenesis inhibitor based on efficacy and safety considerations. Studies show that nature uses the FBPase/PFK cycle as a main control point (metabolic switch) for determining whether the metabolic flux is proceeding in the direction of glycolysis or gluconeogenesis. Claus et al., *Mechanisms of Insulin Action*, Belfrage, P. Editor, pp. 305-321, Elsevier Science, (1992); Regen et al., *J. Theor. Bio.*, 635-658, (1984); Pilkis et al., *Annu. Rev. Biochem.*, 57, 755-783, (1988). FBPase is inhibited by fructose-2,6-bisphosphate in the cell. Fructose-2,6-bisphosphate binds to the substrate site of the enzyme. AMP binds to an allosteric site on the enzyme.

Synthetic FBPase inhibitors have also been reported. Maryanoff has reported that fructose-2,6-bisphosphate analogues inhibit FBPase by binding to the substrate site. *J. Med. Chem.*, 106, 7851, (1984); U.S. Pat. No. 4,968,790, (1984). However, these compounds show relatively low activity and do not inhibit glucose production in hepatocytes, undoubtedly on account of poor cell penetration.

Numerous fructose-1,6-bisphosphatase inhibitors that are useful in the treatment of diabetes have been reported:
  Gruber has reported that some nucleosides can lower blood glucose in the whole animal by inhibition of FBPase (EP 0 427 799 B1). These compounds exert their activity by first performing a phosphorylation to the corresponding monophosphate;
  Gruber et al. (U.S. Pat. No. 5,658,889) have described the use of inhibitors of the AMP site of FBPase for the treatment of diabetes;
  Dan et al. (WO 98/39344, WO 00/014095) have described novel purines and heteroaromatic compounds as FBPase inhibitors;
  Kasibhatla et al. (WO 98/39343) have described novel benzimidazolyl-phosphonates as FBPase inhibitors;
  Reddy et al. (WO 98/39342) have described novel indoles and azaindoles as FBPase inhibitors;
  Jaing et al. (WO 01/047935) have described bisamidate-phosphonates as specific FBPase inhibitors for the treatment of diabetes;
  Bookser et al. (WO 01/066553) have described heterocycle phosphates as specific FBPase inhibitors for the treatment of diabetes.

Imidazolecarboxamide derivatives have previously been described as synthetic intermediates or as anti-inflammatories (cf. EP 1 092 718, FR 2 208 667, FR 2 149 329, FR 2 181 728).

SUMMARY OF THE INVENTION

The present invention relates to novel imidazolecarboxamide derivatives as fructose-1,6-bisphosphatase inhibitors that can be used in the treatment of diabetes and related pathologies.

More particularly, the invention relates to imidazole derivatives of the general formula (I) below:

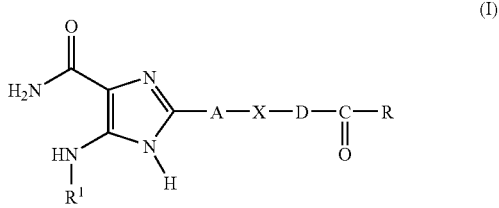

(I)

in which:
R represents a group chosen from: —OH, —OR$^e$ and —NR$^a$R$^b$;
R$^a$ and R$^b$, which may be identical or different, are independently chosen from a hydrogen atom and a radical Z, or alternatively may form, together with the nitrogen atom that bears them, a saturated or unsaturated ring possibly containing from 1 to 3 heteroatoms, or fused or non-fused, bridged or non-bridged rings possibly containing from 1 to 3 heteroatoms, the said ring(s) possibly being substituted by 1 to 3 groups chosen from Y;
R$^e$ represents a group chosen from:
  ($C_1$-$C_8$)alkyl, optionally substituted by one or more groups independently chosen from halogen, ($C_1$-$C_8$)alkyl, ($C_1$-$C_8$)alkoxy, ($C_3$-$C_8$)cycloalkyl and ($C_6$-$C_{14}$)aryl;
  ($C_2$-$C_{20}$)alkenyl, optionally substituted by one or more groups independently chosen from halogen, ($C_1$-$C_8$) alkyl, ($C_1$-$C_8$)alkoxy, ($C_3$-$C_8$)cycloalkyl and ($C_6$-$C_{14}$) aryl;
  ($C_2$-$C_{20}$)alkynyl, optionally substituted by one or more groups independently chosen from halogen, ($C_1$-$C_8$) alkyl, ($C_1$-$C_8$)alkoxy, ($C_3$-$C_8$)cycloalkyl and ($C_6$-$C_{14}$) aryl;
  ($C_3$-$C_8$)cycloalkyl, optionally substituted by one or more groups independently chosen from halogen, ($C_1$-$C_8$) alkyl and ($C_1$-$C_8$)alkoxy;
  ($C_3$-$C_8$) heterocycloalkyl comprising one or more heteroatoms chosen from N, O and S and optionally substituted by one or more groups independently chosen from halogen, ($C_1$-$C_8$)alkyl and ($C_1$-$C_8$)alkoxy;
  ($C_6$-$C_{14}$)aryl, optionally substituted by one or more groups independently chosen from amino, hydroxyl, thio, halogen, ($C_1$-$C_8$)alkyl, ($C_1$-$C_8$)alkoxy, ($C_1$-$C_8$)-alkylthio, ($C_1$-$C_8$)alkylamino, ($C_6$-$C_{14}$)aryl, ($C_6$-$C_{14}$)aryloxy and ($C_6$-$C_{14}$)aryl-($C_1$-$C_8$)alkoxy;
  ($C_6$-$C_{14}$)aryl($C_1$-$C_{20}$)alkyl, optionally substituted by one or more groups independently chosen from amino, hydroxyl, thio, halogen, ($C_1$-$C_8$)alkyl, ($C_1$-$C_8$)-alkoxy, ($C_1$-$C_8$)alkylthio, ($C_1$-$C_8$)alkylamino, ($C_6$-$C_{14}$)aryl, ($C_6$-$C_{14}$)aryloxy and ($C_6$-$C_{14}$)aryl($C_1$-$C_8$)alkoxy;
  ($C_6$-$C_{14}$)heteroaryl, optionally substituted by one or more groups independently chosen from amino, hydroxyl, thio, halogen, ($C_1$-$C_8$)alkyl, ($C_1$-$C_8$)alkoxy, ($C_1$-$C_8$) alkylthio, ($C_1$-$C_8$)alkylamino, ($C_6$-$C_{14}$)aryl, ($C_6$-$C_{14}$) aryloxy and ($C_6$-$C_{14}$)aryl($C_1$-$C_8$)alkoxy; and
  ($C_6$-$C_{14}$)heteroaryl($C_1$-$C_{20}$)alkyl, optionally substituted by one or more groups independently chosen from amino, hydroxyl, thio, halogen, ($C_1$-$C_8$)alkyl, ($C_1$-$C_8$) alkoxy, ($C_1$-$C_8$)alkylthio, ($C_1$-$C_8$)alkylamino, ($C_6$-$C_{14}$) aryl, ($C_6$-$C_{14}$)aryloxy and ($C_6$-$C_{14}$)aryl($C_1$-$C_8$)alkoxy;

$R^1$ represents a group chosen from a hydrogen atom and one of the following groups:

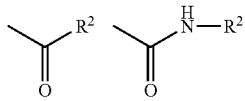

$R^2$ represents a radical Z;

-A-X-D- represents a group in which, independently between A, X and D:

A represents, without preference, a bond or a divalent group obtained after abstraction of a hydrogen atom from a monovalent radical chosen from:
- $(C_1-C_{20})$alkyl, optionally substituted by one or more groups chosen, without preference, from Y;
- $(C_2-C_{20})$alkenyl, optionally substituted by one or more groups chosen, without preference, from Y;
- $(C_2-C_{20})$alkynyl, optionally substituted by one or more groups chosen, without preference, from Y;
- $(C_1-C_{20})$alkoxy, optionally substituted by one or more groups chosen, without preference, from Y;
- $(C_1-C_{20})$alkoxy$(C_1-C_{20})$alkyl, optionally substituted by one or more groups chosen, without preference, from Y;
- $(C_1-C_{20})$alkylthio, optionally substituted by one or more groups chosen, without preference, from Y;
- $(C_1-C_{20})$alkylthio$(C_1-C_{20})$alkyl, optionally substituted by one or more groups chosen, without preference, from Y;
- $(C_1-C_{20})$alkylamino, optionally substituted by one or more groups chosen, without preference, from Y; and
- $(C_1-C_{20})$alkylamino$(C_1-C_{20})$alkyl, optionally substituted by one or more groups chosen, without preference, from Y;

D represents, without preference, a bond or a divalent group obtained after abstraction of a hydrogen atom from a monovalent radical chosen from:
- $(C_1-C_{20})$alkyl, optionally substituted by one or more groups chosen, without preference, from Y;
- $(C_2-C_{20})$alkenyl, optionally substituted by one or more groups chosen, without preference, from Y;
- $(C_2-C_{20})$alkynyl, optionally substituted by one or more groups chosen, without preference, from Y;
- $(C_1-C_{20})$alkoxy$(C_1-C_{20})$alkyl, optionally substituted by one or more groups chosen, without preference, from Y;
- $(C_1-C_{20})$alkylthio$(C_1-C_{20})$alkyl, optionally substituted by one or more groups chosen, without preference, from Y;
- $(C_1-C_{20})$alkylamino$(C_1-C_{20})$alkyl, optionally substituted by one or more groups chosen, without preference, from Y;
- oxy$(C_1-C_{20})$alkyl, optionally substituted by one or more groups chosen, without preference, from Y;
- oxy$(C_1-C_{20})$alkenyl, optionally substituted by one or more groups chosen, without preference, from Y;
- oxy$(C_1-C_{20})$alkynyl, optionally substituted by one or more groups chosen, without preference, from Y;
- thio$(C_1-C_{20})$alkyl, optionally substituted by one or more groups chosen, without preference, from Y;
- thio$(C_1-C_{20})$alkenyl, optionally substituted by one or more groups chosen, without preference, from Y; and
- thio$(C_1-C_{20})$alkenyl, optionally substituted by one or more groups chosen, without preference, from Y;

X represents, without preference, a bond or a divalent group obtained after abstraction of a hydrogen atom from a monovalent radical chosen from:
- $(C_6-C_{14})$aryl, which may itself be optionally substituted by one or more groups chosen independently from Y;
- $(C_5-C_{14})$heteroaryl, which may itself be optionally substituted by one or more groups chosen independently from Y, it being understood that this heteroaryl group may comprise one or more heteroatoms chosen from N, O and S;
- $(C_3-C_8)$cycloalkyl, which may itself be optionally substituted by one or more groups chosen independently from Y;
- $(C_4-C_8)$cycloalkenyl, which may itself be optionally substituted by one or more groups chosen independently from Y; and
- $(C_3-C_8)$heterocycloalkyl, which may itself be optionally substituted by one or more groups independently chosen from Y, it being understood that this heterocycloalkyl group may comprise one or more heteroatoms chosen from N, O and S;

or alternatively,

-A-X-D- represents a single bond;

Y represents a radical chosen from hydroxyl, thio, halogen, cyano, trifluoromethoxy, trifluoromethyl, carboxyl, carboxymethyl or carboxyethyl, $(C_1-C_8)$alkyl, $(C_1-C_8)$alkoxy, $(C_1-C_8)$alkylamino, $(C_6-C_{14})$aryl, $(C_6-C_{14})$arylsulfonyl$(C_1-C_8)$alkyl, $(C_6-C_{14})$aryloxy, $(C_6-C_{14})$aryl$(C_1-C_8)$alkoxy, amino, azido, nitro, guanidino, amidino, phosphono, oxo, carbamoyl, $(C_1-C_8)$alkylsulfonyl, $(C_1-C_8)$alkylsulfinyl, $(C_1-C_8)$alkylthio and $(C_1-C_8)$alkylsulfonyl, two groups Y each borne by two vicinal atoms also possibly forming with these atoms a methylenedioxy group; and Z represents a group chosen from:
- $(C_1-C_{20})$alkyl, optionally substituted by one or more groups chosen, without preference, from Y;
- $(C_2-C_{20})$alkenyl, optionally substituted by one or more groups chosen, without preference, from Y;
- $(C_2-C_{20})$alkynyl, optionally substituted by one or more groups chosen, without preference, from Y;
- $(C_6-C_{14})$aryl or $(C_6-C_{14})$aryl$(C_1-C_{20})$alkyl, $(C_6-C_{14})$aryloxy$(C_1-C_{20})$alkyl, $(C_6-C_{14})$aryl$(C_1-C_{20})$alkoxy$(C_1-C_{20})$alkyl, $(C_6-C_{14})$arylthio$(C_1-C_{20})$alkyl, $(C_6-C_{14})$aryl$(C_1-C_{20})$alkylthio$(C_1-C_{20})$alkyl, the aryl group of each of these groups itself possibly being substituted by one or more groups chosen, without preference, from Y;
- $(C_6-C_{14})$heteroaryl, $(C_6-C_{14})$heteroaryl$(C_1-C_{20})$alkyl, $(C_6-C_{14})$heteroaryloxy$(C_1-C_{20})$alkyl, $(C_6-C_{14})$heteroaryl$(C_1-C_{20})$alkoxy$(C_1-C_{20})$alkyl, $(C_6-C_{14})$heteroarylthio$(C_1-C_{20})$alkyl, $(C_6-C_{14})$heteroaryl$(C_1-C_{20})$alkylthio$(C_1-C_{20})$alkyl, the heteroaryl group of each of these groups itself possibly being substituted by one or more groups chosen, without preference, from Y, it being understood that this heteroaryl group may comprise one or more heteroatoms chosen from N, O and S;
- $(C_3-C_8)$cycloalkyl, $(C_3-C_8)$cycloalkyl$(C_1-C_{20})$alkyl, $(C_3-C_8)$cycloalkyloxy$(C_1-C_{20})$alkyl, $(C_3-C_8)$cycloalkyl$(C_1-C_{20})$alkoxy$(C_1-C_{20})$alkyl, $(C_3-C_8)$cycloalkylthio-$(C_1-C_{20})$alkyl, $(C_3-C_8)$cycloalkyl$(C_1-C_{20})$alkylthio$(C_1-C_{20})$alkyl, the cycloalkyl group of each of these groups itself possibly being substituted by one or more groups chosen, without preference, from Y;
- $(C_3-C_8)$heterocycloalkyl, $(C_3-C_8)$heterocycloalkyl$(C_1-C_{20})$alkyl, $(C_3-C_8)$heterocycloalkyloxy$(C_1-C_{20})$alkyl, $(C_3-C_8)$heterocycloalkyl$(C_1-C_{20})$alkoxy$(C_1-C_{20})$alkyl, $(C_3-C_8)$heterocycloalkylthio$(C_1-C_{20})$alkyl, $(C_3-C_8)$heterocycloalkyl$(C_1-C_{20})$alkylthio$(C_1-C_{20})$alkyl, the heterocycloalkyl group of each of these groups itself possibly being substituted by one or more groups chosen, without preference, from Y, it being understood that this heterocycloalkyl group may comprise one or more heteroatoms chosen from N, O and S;

$(C_6-C_{14})$aryl$(C_2-C_{20})$alkenyl and $(C_6-C_{14})$aryl$(C_2-C_{20})$alkynyl, the aryl group of each of these groups itself possibly being substituted by one or more groups chosen, without preference, from Y; and $(C_6-C_{14})$heteroaryl$(C_2-C_{20})$alkenyl and $(C_6-C_{14})$heteroaryl$(C_2-C_{20})$alkynyl, the heteroaryl group of each of these groups itself possibly being substituted by one or more groups chosen, without preference, from Y, it being understood that this heteroaryl group may comprise one or more heteroatoms chosen from N, O and S.

The invention also relates to the tautomeric forms, the enantiomers, diastereoisomers and epimers and the organic or mineral salts of the compounds of the general formula (I), and also to the crystalline forms, including polymorphisms, of these salts and of the compounds of the formula (I).

The invention also covers the isomers and/or diastereoisomers, in pure form or as a mixture in any proportion of two or more of them, including racemic mixtures.

The compounds of the formula (I) as defined above containing a sufficiently acidic function or a sufficiently basic function or both, may include the corresponding pharmaceutically acceptable salts of organic or mineral acids and/or of organic or mineral bases.

The acid salts are, for example, the hydrochlorides, hydrobromides, sulfates, hydrogen sulfates, dihydrogen phosphates, citrates, maleates, fumarates, trifluoroacetates, 2-naphthalenesulfonates and para-toluenesulfonates.

The bases that can be used for the formation of salts of compounds of the formula (I) are organic or mineral bases. The resulting salts are, for example, the salts formed with metals and especially with alkali metals, alkaline-earth metals and transition metals (such as sodium, potassium, calcium, magnesium or aluminium) or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanoyl and 2-aminoethanol).

The invention also relates to the chiral salts used for the separation of racemates.

By way for example, the following chiral acids are used: (+)-D-di-O-benzoyltartaric acid, (−)-L-di-O-benzoyltartaric acid, (−)-L-di-O,O'-p-toluoyl-L-tartaric acid, (+)-D-di-O,O'-p-toluoyl-L-tartaric acid, (R)-(+)-malic acid, (S)-(−)-malic acid, (+)-camphanic acid, (−)-camphanic acid, R-(−)-1,1'-binaphthalene-2,2'-diylhydrogenophosphonic acid, (+)-camphoric acid, (−)-camphoric acid, (S)-(+)-2-phenylpropionic acid, (R)-(+)-2-phenylpropionic acid, D-(−)-mandelic acid, L-(+)mandelic acid, D-tartaric acid, L-tartaric acid, or a mixture of two or more thereof.

Chiral amines may also optionally be used, for example quinine, brucine, (S)-1-(benzyloxymethyl)propylamine (III), (−)-ephedrine, (4S,5R)-(+)-1,2,2,3,4-tetramethyl-5-phenyl-1,3-oxazolidine, (R)-1-phenyl-2-p-tolylethylamine, (S)-phenylglycinyl, (−)-N-methylephedrine, (+)-(2S,3R)-4-dimethylamino-3-methyl-1,2-diphenyl-2-butanol, (S)-phenylglycinyl or (S)-α-methylbenzylamine, or a mixture of two or more thereof.

The compounds of the formula (I) above also encompass the prodrugs of these compounds.

The term "prodrugs" means compounds which, when administered to the patient, are chemically and/or biologically converted in the live body into compounds of the formula (I).

In the present description, the terms used have the following meanings, unless indicated otherwise:

the term "alkyl" denotes a linear or branched alkyl radical. Among the $(C_1-C_{20})$alkyl radicals that may especially be mentioned, in a non-limiting manner, are methyl, ethyl, propyl, isopropyl, butyl, sec-butyl, tert-butyl, pentyl, hexyl, octyl, decyl, dodecyl, hexadecyl and octadecyl radicals;

the term "alkenyl" denotes a linear or branched hydrocarbon-based radical containing one or more unsaturations in the form of a double bond. $(C_2-C_{20})$Alkenyl radicals that may be mentioned, in a non-limiting manner, include ethenyl, prop-2-enyl, but-2-enyl, but-3-enyl, pent-2-enyl, pent-3-enyl and pent-4-enyl radicals;

the term "alkynyl" denotes a linear or branched hydrocarbon-based radical containing one or more unsaturations in the form of a triple bond, which may optionally also comprise one or more unsaturations in the form of a double bond. $(C_2-C_{20})$Alkynyl radicals that may be mentioned, in a non-limiting manner, include ethynyl, prop-2-ynyl, but-2-ynyl, but-3-ynyl, pent-2-ynyl, pent-3-ynyl and pent-4-ynyl radicals;

the term "alkoxy" refers to the term "alkyl-oxy";

among the "halogens", mention may be made especially of fluorine, chlorine and bromine;

the term "cycloalkyl" denotes an optionally substituted saturated cyclic hydrocarbon-based radical, and comprises mono-, bi- and tricyclic compounds, containing from 3 to 10 carbon atoms. Among the "cycloalkyls" that may especially be mentioned are cyclopropyl, cyclobutyl, cyclopentyl, cyclohexyl, cycloheptyl, cyclooctyl, cyclodecyl and adamantyl radicals, and others, all being optionally substituted;

the term "cycloalkenyl" denotes an optionally substituted mono-, bi- or tricyclic hydrocarbon-based radical comprising at least one unsaturation in the form of a double bond, containing from 3 to 10 carbon atoms. Among the "cycloalkenyls" that may especially be mentioned are cyclopentenyl, cyclopentadienyl, cyclohexenyl, camphenyl and norbornenyl radicals;

in the present invention, the term "heterocycloalkyl" denotes both heterocycloalkyls and heterocycloalkenyls. These radicals are optionally substituted and may be mono-, bi- or tricyclic and comprise one or more heteroatoms preferably chosen from O, S and N, optionally in oxidized form (in the case of S and N), and also optionally one or two double bonds. Preferably, at least one of the rings comprises from 1 to 4 and more preferentially from 1 to 3 endocyclic heteroatoms. Advantageously, a heterocycloalkyl radical comprises one or more rings, each of which is 5- to 8-membered. Examples of heterocycloalkyl radicals are: morpholinyl, piperidyl, piperazinyl, thiazolidinyl, oxazolidinyl, tetrahydrothienyl, dihydrofuryl, tetrahydrofuryl, pyrazolidinyl, 1,3-dioxolanyl, pyrrolidinyl, pyranyl, dihydropyranyl, isoxazolidinyl, imidazolinyl, imidazolidinyl and pyrazolidinyl;

the term "aryl" denotes monocyclic or polycyclic aromatic radicals containing from 5 to 14 ring atoms, and at least one ring contains a system of conjugated pi (π) electrons, including biaryl groups, each of which is possibly substituted. Among the "aryls" that may especially be mentioned are phenyl, naphthyl, biphenyl, anthryl, phenanthryl and indenyl radicals;

the term "heteroaryl" denotes an aromatic heterocyclic radical containing from 5 to 14 endocyclic atoms, among which 1 to 4 atoms are heteroatoms, preferably chosen from oxygen, sulfur and nitrogen. Among the "heteroaryls" that may especially be mentioned are furyl, benzofuryl, thienyl, pyridyl, pyridyl-N-oxide, pyrimidinyl, pyrazinyl, oxazolyl, thiazolyl, isoxazolyl, quinolyl, triazolyl, pyridazinyl, pyrrolyl, imidazolyl, indazolyl, isothiazolyl, indolyl and oxadiazolyl.

In the compounds of the formula (I) as defined above, if $R^a$ and $R^b$ form a ring together with the nitrogen atom that bears them, the said ring is, by way of non-exhaustive example, a morpholine, a piperidine, a piperazine or a pyrrolidine.

According to a first preferred embodiment of the present invention, this invention concerns imidazole derivatives of the general formula (I) as defined above, in which R represents a hydroxyl radical or a radical $R^e$, $R^e$ preferably representing in this case a $(C_1-C_8)$alkyl radical, optionally substituted by one or more groups independently chosen from halogen, $(C_1-C_8)$alkyl, $(C_1-C_8)$alkoxy, $(C_3-C_8)$cycloalkyl and $(C_6-C_{14})$aryl, the other substituents being as defined above, the possible tautomeric forms thereof and the possible enantiomers, diastereoisomers, epimers and organic or mineral salts thereof, and also "prodrugs" thereof.

According to another embodiment of the present invention, this invention preferably relates to the compounds of the formula (I) having one or more of the following characteristics, taken separately or as a combination of two or more of them:

R represents a group chosen from: —OH, —$OR^e$ and —$NR^aR^b$;

$R^a$ and $R^b$, which may be identical or different, are independently chosen from a hydrogen atom and a radical Z, or alternatively may form, together with the nitrogen atom that bears them, a saturated or unsaturated 5- or 6-membered ring possibly containing from 1 to 3 heteroatoms, the said ring possibly being substituted by 1 to 3 groups chosen from Y;

$R^e$ represents a $(C_1-C_8)$alkyl radical, optionally substituted by one or more groups independently chosen from halogen, $(C_1-C_8)$alkyl, $(C_1-C_8)$alkoxy, $(C_3-C_8)$cycloalkyl and $(C_6-C_{14})$aryl;

$R^1$ represents one of the following groups:

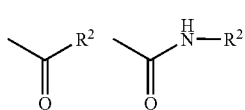

$R^2$ represents a substituted or unsubstituted aryl radical;

-A-X-D- represents a group in which, independently between A, X and D:

A represents a divalent group obtained after abstraction of a hydrogen atom from a $(C_1-C_{20})$alkyl and preferably a $(C_1-C_6)$alkyl radical, optionally substituted by one or more groups chosen, without preference, from Y;

D represents a bond;

X represents a divalent group obtained after abstraction of a hydrogen atom from a monovalent radical chosen from:

$(C_6-C_{14})$aryl, which may itself be optionally substituted by one or more groups chosen, without preference, from Y;

$(C_5-C_{14})$heteroaryl, which may itself be optionally substituted by one or more groups chosen, without preference, from Y, it being understood that this heteroaryl group may comprise one or more heteroatoms chosen from N, O and S;

$(C_3-C_8)$cycloalkyl, which may itself be optionally substituted by one or more groups chosen, without preference, from Y;

$(C_4-C_8)$cycloalkenyl, which may itself be optionally substituted by one or more groups chosen, without preference, from Y; and $(C_3-C_8)$heterocycloalkyl, which may itself be optionally substituted by one or more groups chosen, without preference, from Y, it being understood that this heterocycloalkyl group may comprise one or more heteroatoms chosen from N, O and S;

Y represents a radical chosen from hydroxyl, thio, halogen, cyano, trifluoromethoxy, trifluoromethyl, carboxyl, carboxymethyl or carboxyethyl, $(C_1-C_8)$alkyl, $(C_1-C_8)$alkoxy, $(C_1-C_8)$alkylamino, $(C_6-C_{14})$aryl, $(C_6-C_{14})$aryloxy, $(C_6-C_{14})$aryl$(C_1-C_8)$alkoxy, amino, oxo and carbamoyl; and Z represents a group chosen from:

$(C_1-C_{20})$alkyl and preferably $(C_1-C_6)$alkyl, optionally substituted by one or more groups chosen, without preference, from Y;

$(C_2-C_{20})$alkenyl and preferably $(C_2-C_6)$alkenyl, optionally substituted by one or more groups chosen, without preference, from Y;

$(C_6-C_{14})$aryl or $(C_6-C_{14})$aryl$(C_1-C_{20})$alkyl, the aryl group of each of these groups itself possibly being substituted by one or more groups chosen, without preference, from Y; and $(C_6-C_{14})$heteroaryl or $(C_6-C_{14})$heteroaryl$(C_1-C_{20})$alkyl, the heteroaryl group of each of these groups itself possibly being substituted by one or more groups chosen, without preference, from Y, it being understood that this heteroaryl group may comprise one or more heteroatoms chosen from N, O and S, the possible tautomeric forms thereof and the possible enantiomers, diastereoisomers, epimers and organic or mineral salts thereof, and also "prodrugs" thereof.

According to another embodiment of the present invention, the invention preferably relates to the compounds of the formula (I) having the following characteristics:

R represents a group chosen from: —OH, —$OR^e$ and —$NR^aR^b$; and $R^a$ and $R^b$, which may be identical or different, are independently chosen from a hydrogen atom and a radical Z, or alternatively may form, together with the nitrogen atom that bears them, a saturated or unsaturated 5- or 6-membered ring possibly containing from 1 to 3 heteroatoms, the said ring possibly being substituted by 1 to 3 groups chosen from Y; and $R^e$ represents a $(C_1-C_8)$alkyl radical, optionally substituted by one or more groups independently chosen from halogen, $(C_1-C_8)$alkyl, $(C_1-C_8)$alkoxy, $(C_3-C_8)$cycloalkyl and $(C_6-C_{14})$aryl; and $R^1$ represents one of the following groups:

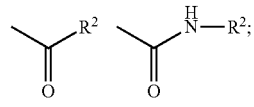

R² represents an aryl radical; and

-A-X-D- represents a group in which, independently between A, X and D:

A represents a divalent group obtained after abstraction of a hydrogen atom from a (C₁-C₂₀)alkyl and preferably a (C₁-C₆)alkyl radical, optionally substituted by one or more groups chosen, without preference, from Y; and D represents a bond; and X represents a divalent group obtained after abstraction of a hydrogen atom from a monovalent radical chosen from:

(C₆-C₁₄)aryl, which may itself be optionally substituted by one or more groups chosen, without preference, from Y;

(C₅-C₁₄)heteroaryl, which may itself be optionally substituted by one or more groups chosen, without preference, from Y, it being understood that this heteroaryl group may comprise one or more heteroatoms chosen from N, O and S;

(C₃-C₈)cycloalkyl, which may itself be optionally substituted by one or more groups chosen, without preference, from Y;

(C₄-C₈)cycloalkenyl, which may itself be optionally substituted by one or more groups chosen, without preference, from Y; and (C₃-C₈)heterocycloalkyl, which may itself be optionally substituted by one or more groups chosen, without preference, from Y, it being understood that this heterocycloalkyl group may comprise one or more heteroatoms chosen from N, O and S; and Y represents a radical chosen from hydroxyl, thio, halogen, cyano, trifluoromethoxy, trifluoromethyl, carboxyl, carboxymethyl or carboxyethyl, (C₁-C₈)alkyl, (C₁-C₈)alkoxy, (C₁-C₈)alkylamino, (C₆-C₁₄)aryl, (C₆-C₁₄)aryloxy, (C₆-C₁₄)aryl(C₁-C₈)alkoxy, amino, oxo and carbamoyl; and Z represents a group chosen from:

(C₁-C₂₀)alkyl and preferably (C₁-C₆)alkyl, optionally substituted by one or more groups chosen, without preference, from Y;

(C₂-C₂₀)alkenyl and preferably (C₂-C₆)alkenyl, optionally substituted by one or more groups chosen, without preference, from Y;

(C₆-C₁₄)aryl or (C₆-C₁₄)aryl(C₁-C₂₀)alkyl, the aryl group of each of these groups itself possibly being substituted by one or more groups chosen, without preference, from Y; and (C₆-C₁₄)heteroaryl or (C₆-C₁₄)heteroaryl(C₁-C₂₀)alkyl, the heteroaryl group of each of these groups itself possibly being substituted by one or more groups chosen, without preference, from Y, it being understood that this heteroaryl group may comprise one or more heteroatoms chosen from N, O and S, the possible tautomeric forms thereof and the possible enantiomers, diastereoisomers, epimers and organic or mineral salts thereof, and also "prodrugs" thereof.

According to yet another preferred embodiment, the invention relates to imidazolecarboxamide derivatives chosen from:

5-[5-(4-tert-butylbenzoylamino)-4-carbamoyl-1H-imidazol-2-ylmethyl]-furan-2-carboxylic acid;

5-[4-carbamoyl-5-(4-propylbenzoylamino)-1H-imidazol-2-ylmethyl]furan-2-carboxylic acid;

5-{4-carbamoyl-5-[3-(4-pentylphenyl)ureido]-1H-imidazol-2-ylmethyl}-furan-2-carboxylic acid;

5-{4-carbamoyl-5-[3-(2,6-diisopropylphenyl)ureido]-1H-imidazol-2-yl-methyl}furan-2-carboxylic acid;

5-{5-[3-(4-butylphenyl)ureido]-4-carbamoyl-1H-imidazol-2-ylmethyl}furan-2-carboxylic acid;

5-{4-carbamoyl-5-[3-(3-phenoxyphenyl)ureido]-1H-imidazol-2-ylmethyl}-furan-2-carboxylic acid;

5-[4-carbamoyl-5-(4-propylbenzoylamino)-1H-imidazol-2-ylmethyl]thiophene-2-carboxylic acid; and 5-(4-tert-butylbenzoylamino)-2-[5-(pyrrolidine-1-carbonyl)furan-2-yl-methyl]-1H-imidazole-4-carboxamide, the possible tautomeric forms thereof and the possible enantiomers, diastereoisomers, epimers and organic or mineral salts thereof, and also "prodrugs" thereof.

The compounds of the general formula (I) can be prepared according to the following process. The synthetic intermediates leading to the compounds of the general formula (1) as described above are either commercially available, or can be prepared directly according to known processes (or after adaptations of known processes) that are available in the scientific literature or patents and patent applications or from Chemical Abstracts, online databases or the Internet.

Thus, another subject of the present invention relates to a process for the preparation of the compounds of the formula (I) as defined above, according to the general method described below:

Step 1

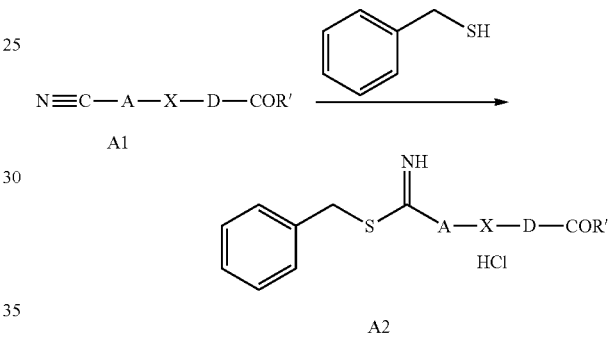

Step 2

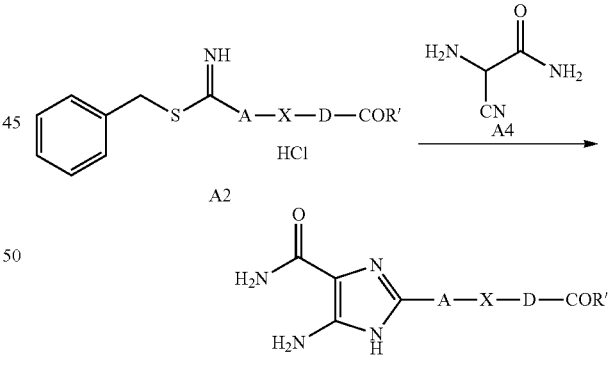

The synthesis of compound A2, in which A, X and D are as described above, R' having the same definition as R defined above, with the exception of the hydroxyl radical, can be prepared via the action of a mercaptan derivative, preferably benzyl mercaptan, on a nitrile derivative chosen from A1, in which A, X, D and R' are as described above, in a solvent, such as dichloromethane in the presence of hydrochloric acid introduced in gaseous form into the reaction medium.

The reaction can be performed at a temperature ranging from −10° C. to 25° C. and preferably from 0 to 10° C., over a period possibly ranging from 1 hour to 72 hours.

Compound A3, in which A, X, D and R' are as described above, is obtained by reacting the thio imino ether A2 with the aminocyanoacetamide A4, in a solvent, such as ethanol or methanol, in the presence of a base, such as sodium hydrogen carbonate. The reaction can be performed at a temperature ranging from room temperature to the boiling point of the solvent under consideration.

Compound A3 can be optionally subjected to a deprotection reaction, under standard conditions known to those skilled in the art, according to the following scheme:

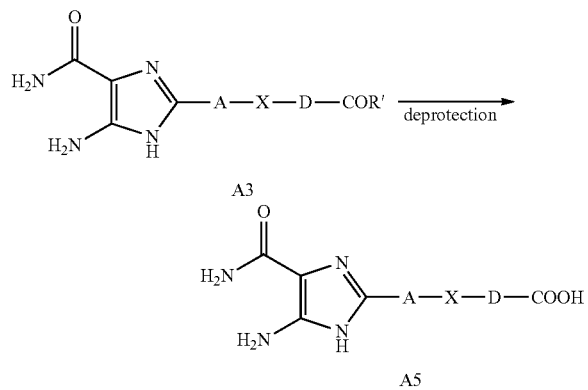

to give compound A5, in which A, D and X are as defined above, the compounds of the formulae A3 and A5 forming the set of compounds of the formula (I) in which $R^1$ represents a hydrogen atom.

Step 3

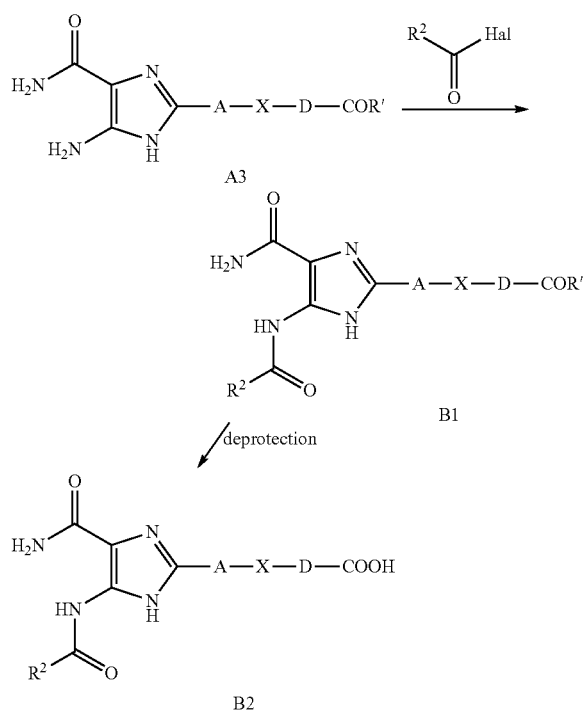

Compound B1, in which A, D, X, R' and $R^2$ are as described above, can be obtained via the action of an acid halide of the formula Hal-CO—$R^2$, in which $R^2$ is as defined above, on compound A3, in the presence of an organic base, such as, in a non-limiting manner, triethylamine, pyridine or diisopropylethylamine, in a solvent, such as acetonitrile, toluene, dichloromethane or tetrahydrofuran.

A mineral base, such as, in a non-limiting manner, sodium hydrogen carbonate or caesium carbonate can also be used. These derivatives of amide type can also be obtained via the known acid-activation methods, using coupling agents, such as carbonyldiimidazole or, in a non-limiting manner, HOBt or PyBOP.

Compound B2 is obtained using known deprotection methods and, in this respect, mention may especially be made of the use of aqueous sodium hydroxide solution in the presence or absence of additional solvents, such as ethanol, methanol or tetrahydrofuran.

In the case of a tert-butyl ester, trifluoroacetic acid can be used.

The compounds of the formulae B1 and B2 form the set of compounds of the formula (I) as defined above in which $R^1$ represents the group:

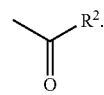

The compounds of the formula (I) in which $R^1$ represents the group

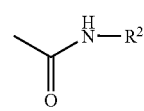

can be obtained according to the following reaction scheme:

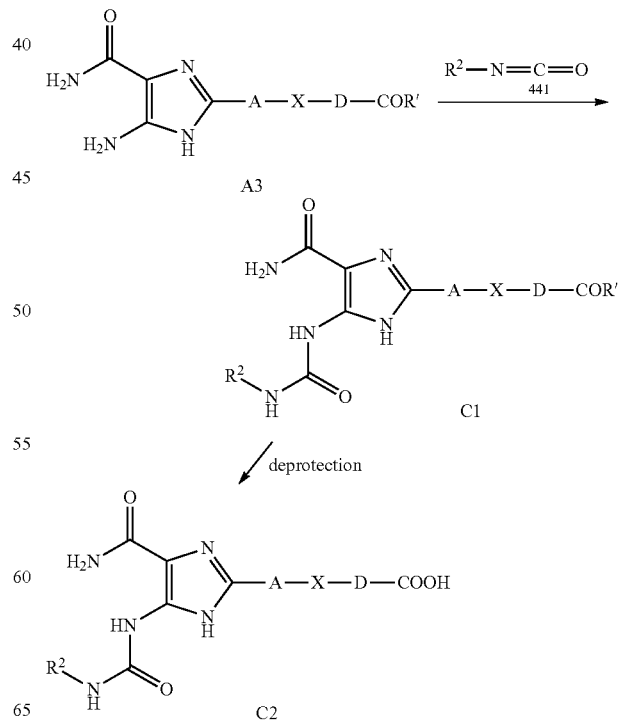

Compound C1, in which A, D, X, R' and $R^2$ are as defined above, can be obtained via the action of the isocyanate of the formula $R^2$—N=C=O, on compound A3 defined above, in a solvent, such as acetonitrile, toluene, dichloromethane or tetrahydrofuran.

The reaction can be performed at a temperature ranging from 0° C. to the boiling point of the solvent used.

Compound C2, in which A, D, X and $R^2$ are as defined above, is obtained using known deprotection methods, especially using aqueous sodium hydroxide solution in the presence or absence of additional solvents, such as ethanol, methanol or THF.

The compounds of the formulae C1 and C2 form the set of compounds of the formula (I) as defined above, in which $R^1$ represents the group:

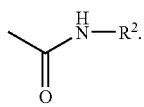

According to one variant, the compounds of the formula (I) for which R represents the group —$NR^aR^b$ can advantageously be obtained from the compounds B2 and C2 as defined above, according to the following reaction schemes:

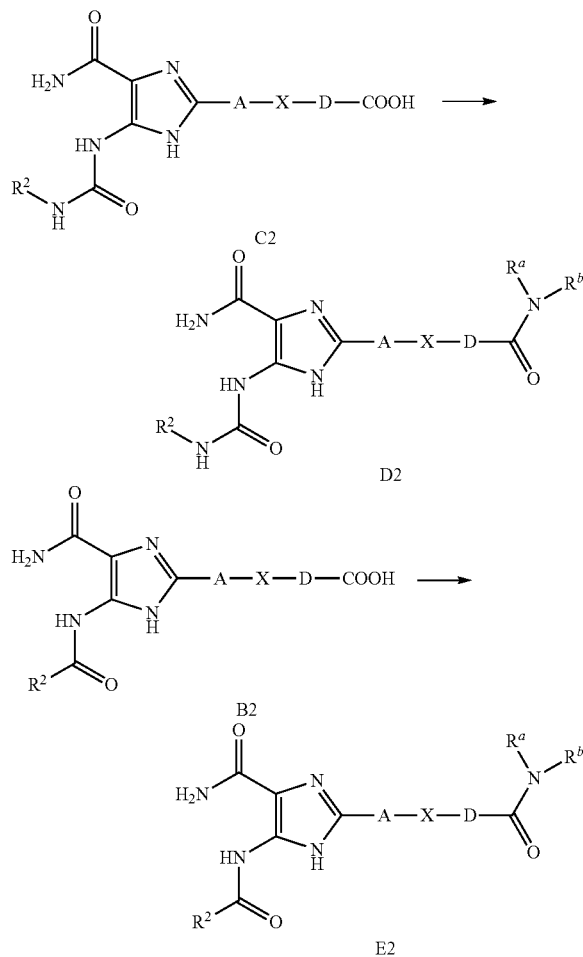

The amide derivatives D2 and E2 can be obtained especially from the acids C2 and B2, respectively, via conventional means. By way of example, the acid chloride under consideration can be reacted with an amine. The desired amides can be obtained using mixed anhydride techniques; coupling agents, such as, in a non-limiting manner, carbonyldiimidazole and carbodiimides, such as dicyclohexylcarbodiimide can also be used. Coupling agents, such as HOBt [1-hydroxybenzotriazole] or PyBOP [(benzotriazol-1-yloxy) tris-(pyrrolidino)phosphonium hexafluorophosphate] can also be used.

The compounds of the invention as defined above show hypoglycaemiant activity and, in this respect, are useful in the treatment of pathologies associated with insulin resistance syndrome.

Specifically, insulin resistance is characterized by a reduction in the action of insulin (cf. «Presse Médicale», (1997), 26(14), 671-677) and is involved in a large number of pathological states, such as diabetes and more particularly non-insulin-dependent diabetes (type II diabetes or NIDDM), dyslipidaemia, obesity, arterial hypertension and also certain microvascular and macrovascular complications, for instance atherosclerosis, retinopathy and neuropathy.

In this respect, reference will be made, for example, to Diabetes, 37, (1988), 1595-1607; Journal of Diabetes and its complications 12, (1998), 110-119 or Horm. Res., 38, (1992), 28-32.

A subject of the present invention is thus also pharmaceutical compositions comprising, as active principle, at least one compound according to the invention.

The pharmaceutical compositions according to the invention can be in forms intended for parenteral, oral, rectal, permucous or percutaneous administration.

They will thus be in the form of injectable solutions or suspensions or multi-dose bottles, in the form of plain or coated tablets, sugar-coated tablets, wafer capsules, gel capsules, pills, cachets, powders, suppositories or rectal capsules, or solutions or suspensions, for percutaneous use in a polar solvent, or for permucous use.

The excipients that are suitable for such administrations are pharmaceutically acceptable excipients, for instance cellulose or microcrystalline cellulose derivatives, alkaline-earth metal carbonates, magnesium phosphate, starches, modified starches and lactose for the solid forms.

Cocoa butter or polyethylene glycol stearates are the preferred excipients for rectal use.

Water, aqueous solutions, physiological saline or isotonic solutions are the vehicles most conveniently used for parenteral use.

For example, if the compounds according to the present invention are administered orally, in the form of plain or coated tablets, sugar-coated tablets, wafer capsules, gel capsules, pills, cachets or powders, the dosage can range between about 0.1 mg/kg and about 100 mg/kg, preferably between about 0.5 mg/kg and about 50 mg/kg, more preferably between 1 mg/kg and 10 mg/kg and most preferably between about 2 mg/kg and about 5 mg/kg.

Assuming that the weight of the patient to be treated can range between 10 kg and 100 kg, and according to the dosage mentioned above, the daily intakes can be between about 1 to 10 mg/day and about 1000 to 10 000 mg/day, preferably between about 5 to 50 mg/day and about 500 to 5000 mg/day, more preferably between about 10 to 100 mg/day and about 100 to 1000 mg/day and most preferably between about 20 to 200 mg/day and about 50 to 500 mg/day.

As indicated above, the formulations of the present invention that are suitable for oral administration can be in the form of individual doses, such as tablets, cachets or sugar-coated tablets, each comprising a predetermined amount of active material; the formulations can also be in the form of powder or granules, in the form of a solution or a suspension in an aqueous or non-aqueous medium, or alternatively in the form of a liquid emulsion of oil-in-water type or in the form of a liquid emulsion of water-in-oil type. The active material can also be administered in the form of a bolus, paste or electuary.

In the case of non-insulin-dependent diabetes, in man, hyperglycaemia is the result of two major defects: an impairment in insulin secretion and a reduction in the efficacy of insulin at three sites, namely the liver, the muscles and the adipose tissue.

By inhibiting gluconeogenesis via inhibition of the key enzyme fructose-1,6-bisphosphatase, the compounds of the present invention are thus capable of improving the glycaemia of non-insulin-dependent diabetic patients.

Thus, and according to another aspect, the present invention relates to the use of at least one compound of the general formula (I), the possible tautomeric forms thereof and the possible enantiomers, diastereoisomers, epimers and organic or mineral salts thereof, and also "prodrugs" thereof, for the treatment or prevention of pathologies associated with excessive glycogen storage or diseases, such as cardiovascular diseases, including atherosclerosis, myocardial ischaemic accidents, for the treatment of or preventing type II diabetes and diseases associated with metabolic disorders, such as hypercholesterolaemia or hyperlipidaemia, which are exacerbated by hyperinsulinemia and hyperglycaemia.

The examples that follow illustrate the invention without, however, limiting it. The starting materials used are known products or are prepared according to known procedures.

The percentages are expressed on a weight basis, unless otherwise mentioned.

The compounds were characterized especially via the following analytical techniques:

The NMR spectra were acquired using a Brüker Avance DPX 200 MHz NMR spectrometer or a Brüker Avance DPX 500 MHz spectrometer.

The masses were determined by HPLC coupled to an Agilent Series 1100 mass detector.

The melting points (m.p.) were measured on a Köfler Leica VMBH block.

Production of the Imidazolecarboxamide Synthetic Intermediates

EXAMPLE 1

Ethyl 5-chloromethylfuran-2-carboxylate

To a solution of 100 g (0.71 M) of ethyl 2-furoate in 250 ml of dichloromethane are added 30.6 g (1.02 M) of paraformaldehyde and 25.4 g (0.19 M) of zinc chloride. Gaseous hydrogen chloride is passed into the reaction medium. An exothermic reaction is observed, and the temperature reaches 35° C. The evolution of gas is maintained up to the end of the reaction, which is monitored by thin-layer chromatography (TLC). The product obtained is then purified by chromatography on silica using dichloromethane as eluent, to give 134.6 g of ethyl 5-chloromethylfuran-2-carboxylate in the form of a colourless oil.

Yield: 98%.

$^1$H NMR (200 MHz/DMSO-d6) δ (ppm): 1.28 (t, 3H); 4.27 (d, 2H); 4.51 (s, 2H); 6.39 (d, 1H); 7.02 (d, 1H).

EXAMPLE 2

Ethyl 5-cyanomethylfuran-2-carboxylate

To a solution of 131.3 g (0.7 M) of ethyl 5-chloromethylfuran-2-carboxylate in 280 ml of ethanol is added a solution of 68 g of potassium cyanide (1.04 M) and 13.7 g (0.15 M) of CuCN in 140 ml of demineralized water. The reaction medium is heated at 40° C. with stirring for 18 hours. A further 68 g of potassium cyanide (1.04 M) and 13.7 g (0.15 M) of CuCN in 140 ml of demineralized water are added to the reaction medium, which is maintained at 40° C. with stirring for a further 18 hours.

Water is then added and the aqueous phase is extracted three times with diethyl ether. The combined organic phases are washed twice with water and then dried over sodium sulfate and concentrated under vacuum. The oil obtained is purified by chromatography on silica using dichloromethane as eluent, to obtain 94.6 g of ethyl 5-cyanomethylfuran-2-carboxylate in the form of a colourless oil.

Yield: 76%.

$^1$H NMR (200 MHz/DMSO-d6) δ (ppm): 1.36 (t, 3H); 4.36 (q, 2H); 4.41 (s, 2H); 6.68 (d, 1H); 7.36 (d, 1H).

EXAMPLE 3

Ethyl 5-benzylsulfanylcarbonimidoylmethylfuran-2-carboxylate hydrochloride

Gaseous hydrogen chloride is passed for 30 minutes at 10° C. through a solution of 94.5 g (0.53 M) of ethyl 5-cyanomethylfuran-2-carboxylate and 61.9 ml (0.53 M) of benzyl mercaptan in 2000 ml of diethyl ether.

After evaporating under vacuum, the residue is taken up in fresh diethyl ether, and a solid crystallizes, which is isolated by filtration, to give 30.5 g of ethyl 5-benzylsulfanylcarbonimidoylmethylfuran-2-carboxylate in the form of a solid, which is used without further purification in the following step.

Production of the Compounds According to the Invention

EXAMPLE 4

Ethyl 5-(5-amino-4-carbamoyl-1H-imidazol-2-ylmethyl)furan-2-carboxylate 30.5 g (0.09 M) of ethyl 5-benzylsulfanylcarbonimidoylmethylfuran-2-carboxylate, 8.9 g (0.09 M) of aminocyanoacetamide and 7.5 g (0.09 M) of sodium hydrogen carbonate in 180 ml of methanol are refluxed with stirring for 5 hours. The crude product obtained is purified by chromatography on silica using a dichloromethane/methanol mixture (90/10) as eluent, to give 17 g of ethyl 5-(5-amino-4-carbamoyl-1H-imidazol-2-ylmethyl)furan-2-carboxylate in the form of a vitreous brown solid.

$^1$H NMR (200 MHz/DMSO-d6) δ (ppm): 1.29 (t, 3H); 4.03 (s, 2H); 4.30 (q, 2H); 5.58 (s, 2H); 6.46 (s, 1H); 6.72 (s, 2H); 7.26 (s, 1H); 11.47 (s, 1H).

By way of example, the following compounds are prepared, optionally with minor modifications, according to the procedure described in Example 4:

EXAMPLE 4.2

Ethyl [4-(5-amino-4-carbamoyl-1H-imidazol-2-yl)phenyl]acetate

Empirical formula: $C_{14}H_{16}N_4O_3$=288.3;

Mass spectrum: 289.1 (M+).

EXAMPLE 4.3

Methyl 4-(5-amino-4-carbamoyl-1H-imidazol-2-yl)benzoate

Empirical formula: $C_{12}H_{12}N_4O_3$=260.49;

Mass spectrum: 261 (M+).

EXAMPLE 4.4

Methyl [4-(5-amino-4-carbamoyl-1H-imidazol-2-ylmethoxy)phenyl]acetate

Empirical formula: $C_{14}H_{16}N_4O_4$=304.29;
Mass spectrum: 305.1 (M+).

EXAMPLE 4.5

Ethyl 5-(5-amino-4-carbamoyl-1H-imidazol-2-yl)thiophene-2-carboxylate

Empirical formula: $C_{11}H_{12}N_4O_3S$=280.3;
Mass spectrum: 279 (M−).

EXAMPLE 4.6

Ethyl 5-(5-amino-4-carbamoyl-1H-imidazol-2-ylmethyl)thiophene-2-carboxylate

Empirical formula: $C_{12}H_{14}N_4O_3S$=294.33
Mass spectrum: 293 (M−).

EXAMPLE 4.7

Methyl 5-(5-amino-4-carbamoyl-1H-imidazol-2-yl)furan-2-carboxylate

EXAMPLE 4.8

Methyl 4-(5-amino-4-carbamoyl-1H-imidazol-2-ylmethyl)benzoate

EXAMPLE 4.9

Ethyl [4-(5-amino-4-carbamoyl-1H-imidazol-2-ylmethyl)phenoxy]acetate

EXAMPLE 4.10

Ethyl [4-(5-amino-4-carbamoyl-1H-imidazol-2-yl)phenoxy]acetate

Production of the Derivatives of Acylamino Type

EXAMPLE 5

Ethyl 5-[4-carbamoyl-5-(4-propylbenzoylamino)-1H-imidazol-2-ylmethyl]-furan-2-carboxylate 4-Propylbenzoyl chloride (2 ml; 11.9 mM) are added dropwise to 3 g (10.8 mM) of ethyl 5-(5-amino-4-carbamoyl-1H-imidazol-2-ylmethyl)furan-2-carboxylate and 1.8 g of sodium hydrogen carbonate (21.6 mM) in 15 ml of THF. The reaction medium is then stirred at 20° C. for 20 hours. After addition of water, a solid precipitate is formed, which is isolated and purified by chromatography on silica, first using a dichloromethane/acetone mixture (90/10) as eluent, and then a dichloromethane/methanol mixture (90/10) to give 2.9 g of ethyl 5-[4-carbamoyl-5-(4-propylbenzoylamino)-1H-imidazol-2-ylmethyl]furan-2-carboxylate in the form of a white solid.
Yield: 57%.
$^1$H NMR (200 MHz/DMSO-d6) δ (ppm): 0.77 (t, 3H); 1.13 (t, 3H); 1.51 (m, 2H); 2.55 (m, 2H); 4.14 (s+m, 4H); 6.30 (s, 1H); 7.08 (m, 3H); 7.31 (d, 2H); 7.71 (d, 2H); 11.08 (s, 1H); 12.74 (s, 1H).
m.p.: 184-186° C.

EXAMPLE 6

5-[4-Carbamoyl-5-(4-propylbenzoylamino)-1H-imidazol-2-ylmethyl]furan-2-carboxylic acid 1.8 g (4.24 mM) of ethyl 5-[4-carbamoyl-5-(4-propylbenzoylamino)-1H-imidazol-2-ylmethyl]furan-2-carboxylate are added to 10 ml of an ethanol/THF mixture (50-50). 4 ml of aqueous 3N sodium hydroxide solution are then added and the reaction medium is maintained at 40° C. with stirring for 2 hours. The reaction medium is allowed to cool and is acidified with acetic acid; a solid crystallizes. The solid is filtered off and washed with demineralized water to give, after drying, 1.7 g of 5-[4-carbamoyl-5-(4-propylbenzoylamino)-1H-imidazol-2-ylmethyl]furan-2-carboxylic acid.
Yield: 95%.
$^1$H NMR (500 MHz/DMSO-d6) δ (ppm): 1.39 (t, 3H); 1.66 (m, 2H); 2.78 (t, 2H); 6.55 (s, 1H); 7.22 (s, 1H); 7.43 (d, 2H); 7.93 (d, 2H); 11.22 (s, 1H); 12.85 (s, 1H).

By way of example, the following compounds are prepared, optionally with minor modifications, according to the procedures described in Examples 5 and 6:

EXAMPLE 6.2

5-[4-Carbamoyl-5-(4-chlorobenzoylamino)-1H-imidazol-2-yl]furan-2-carboxylic acid $^1$H NMR (500 MHz/DMSO-d6) δ (ppm): 6.64 (s, 1H); 6.84 (s, 1H); 7.57 (m, 2H); 7.96 (d, 2H).

EXAMPLE 6.3

{4-[4-Carbamoyl-5-(4-pentylbenzoylamino)-1H-imidazol-2-ylmethyl]-phenoxy}acetic acid $^1$H NMR (500 MHz/DMSO-d6) δ (ppm): 0.87 (t, 3H); 1.31 (m, 4H); 1.67 (m, 2H); 2.63 (t, 2H); 4.26 (s, 2H); 4.68 (s, 2H); 6.96 (d, 2H); 7.34 (d, 2H); 7.43 (d, 2H); 7.94 (d, 2H).

EXAMPLE 6.4

{4-[4-Carbamoyl-5-(4-ethylbenzoylamino)-1H-imidazol-2-yl]phenyl}acetic acid
$^1$H NMR (500 MHz/DMSO-d6) δ (ppm): 1.25 (t, 3H); 2.74 (q, 2H); 3.75 (s, 2H); 7.45 (d, 2H); 7.55 (d, 2H); 8.00 (d, 2H); 8.08 (d, 2H).

EXAMPLE 6.5

4-(4-Aminomethyl-5-isobutyrylamino-1H-imidazol-2-ylmethyl)benzoic acid $^1$H NMR (500 MHz/DMSO-d6) δ (ppm): 1.12 (s, 3H); 1.15 (s, 3H); 2.67 (m, 1H); 4.07 (s, 2H); 7.14 (m, 2H); 7.32 (d, 2H); 7.87 (d, 2H); 10.18 (s, 1H); 12.55 (s, 1H).

EXAMPLE 6.8

5-[5-(4-tert-Butylbenzoylamino)-4-carbamoyl-1H-imidazol-2-ylmethyl]furan-2-carboxylic acid

EXAMPLE 6.9

5-[5-(4-Butylbenzoylamino)-4-carbamoyl-1H-imidazol-2-ylmethyl]thiophene-2-carboxylic acid

EXAMPLE 6.10

{4-[4-Carbamoyl-5-(2-methyl benzoylamino)-1H-imidazol-2-yl]phenyl}acetic acid

EXAMPLE 6.11

{4-[4-Carbamoyl-5-(4-fluorobenzylamino)-1H-imidazol-2-yl]phenyl}acetic acid

EXAMPLE 6.12

[4-(5-Benzoylamino-4-carbamoyl-1H-imidazol-2-yl)phenoxy]acetic acid

EXAMPLE 6.13

{4-[4-Carbamoyl-5-(4-methylbenzoylamino)-1H-imidazol-2-ylmethoxy]-phenyl}acetic acid

EXAMPLE 6.14

5-(5-Benzoylamino-4-carbamoyl-1H-imidazol-2-yl)furan-2-carboxylic acid

EXAMPLE 6.15

5-[4-Carbamoyl-5-(4-fluorobenzylamino)-1H-imidazol-2-ylmethyl]thiophene-2-carboxylic acid

EXAMPLE 6.16

{4-[5-(4-Butylbenzoylamino)-4-carbamoyl-1H-imidazol-2-ylmethyl]phenoxy}acetic acid Production of the Derivatives of Urea Type

EXAMPLE 7

5-{4-Carbamoyl-5-[3-(4-methylbenzyl)ureido]-1H-imidazol-2-ylmethyl}-furan-2-carboxylic acid 116.3 mg (0.79 mM) of 4-methylbenzyl isocyanate are added to 200 mg (0.72 mM) of ethyl 5-(5-amino-4-carbamoyl-1H-imidazol-2-ylmethyl)-furan-2-carboxylate in 2 ml of THF. The reaction medium is then stirred at 20° C. for 20 hours. After addition of water, the mixture is extracted with ethyl acetate. After evaporating under vacuum, an oil is obtained. The ester thus obtained is treated with aqueous 1N sodium hydroxide solution in 2 ml of a THF/ethanol mixture (50/50) at 20° C. for 16 hours. After addition of water, a solid precipitates.

The solid is filtered off and washed with water to give 131.7 mg of 5-{4-carbamoyl-5-[3-(4-methylbenzyl)ureido]-1H-imidazol-2-ylmethyl}furan-2-carboxylic acid.

Yield: 46%.

$^1$H NMR (500 MHz/DMSO-d6+TFA) δ (ppm): 2.3 (s, 3H); 4.31 (s, 2H); 4.57 (s, 2H); 6.59 (d, 1H); 7.18 (d, 2H); 7.22 (d, 3H).

By way of example, the following compounds are prepared, optionally with minor modifications, according to the procedures described in Example 7:

EXAMPLE 7.2

Methyl [4-(4-carbamoyl-5-{3-[2-(2,3-dimethoxyphenyl)ethyl]ureido}-1H-imidazol-2-ylmethoxy)phenyl]acetate $^1$H NMR (200 MHz/DMSO-d6) δ (ppm): 2.73 (m, 2H); 3.27 (m, 2H); 3.58 (m, 5H); 3.70 (s, 3H); 3.76 (s, 3H); 5.95 (s, 2H); 6.98 (m, 9H); 7.75 (s, 1H); 9.24 (s, 1H); 12.44 (s, 1H).

EXAMPLE 7.3

Methyl (4-{4-carbamoyl-5-[3-(3,4-dimethylphenyl)ureido]-1H-imidazol-2-yl-methoxy}phenyl)acetate Empirical formula: $C_{23}H_{25}N_5O_5$=451.47;
Mass spectrum: 450 (M+).

EXAMPLE 7.4

Ethyl 5-{4-carbamoyl-5-[3-(4-pentylphenyl)ureido]-1H-imidazol-2-ylmethyl}-furan-2-carboxylate Empirical formula: $C_{24}H_{29}N_5O_5$=467.52;
Mass spectrum: 466 (M−).

EXAMPLE 7.5

4-{4-Carbamoyl-5-[3-(4-trifluoromethylphenyl)ureido]-1H-imidazol-2-yl}-benzoic acid $^1$H NMR (500 MHz/DMSO-d6 after exchange) δ (ppm): 7.70 (d, 2H); 7.80 (d, 2H); 8.12 (d, 2H); 8.20 (d, 2H).

EXAMPLE 7.6

4-{4-Carbamoyl-5-[3-(3,4-dimethoxyphenyl)ureido]-1H-imidazol-2-yl-methyl}benzoic acid $^1$H NMR (500 MHz/DMSO-d6) δ (ppm): 3.75 (s, 3H); 3.8 (s, 3H); 6.93 (m, 2H); 7.25 (s, 1H); 7.52 (d, 2H); 7.97 (d, 2H); 9.80 (s, 1H); 12.30 (s, 1H).

EXAMPLE 7.7

(4-{4-Carbamoyl-5-[3-(4-chlorophenyl)ureido]-1H-imidazol-2-yl}phenyl)-acetic acid $^1$H NMR (500 MHz/DMSO-d6) δ (ppm): 3.70 (s, 2H); 7.07 (s, 1H); 7.38 (d, 2H); 7.52 (d, 2H); 7.60 (d, 2H); 8.10 (d, 2H); 9.1 (s, 2H); 11.4 (s, 1H).

EXAMPLE 7.8

5-{4-Carbamoyl-5-[3-(4-pentylphenyl)ureido]-1H-imidazol-2-ylmethyl}furan-2-carboxylic acid

EXAMPLE 7.9

5-{4-Carbamoyl-5-[3-(2,6-diisopropylphenyl)ureido]-1H-imidazol-2-yl-methyl}furan-2-carboxylic acid

EXAMPLE 7.10

5-{5-[3-(4-Butylphenyl)ureido]-4-carbamoyl-1H-imidazol-2-ylmethyl}furan-2-carboxylic acid

EXAMPLE 7.11

5-{5-[3-(4-Butylphenyl)ureido]-4-carbamoyl-1H-imidazol-2-yl}furan-2-carboxylic acid

EXAMPLE 7.12

5-{4-Carbamoyl-5-[3-(3-phenoxyphenyl)ureido]-1H-imidazol-2-ylmethyl}-furan-2-carboxylic acid

EXAMPLE 7.13

5-{4-Carbamoyl-5-[3-(4-trifluoromethylphenyl)ureido]-1H-imidazol-2-yl-methyl}furan-2-carboxylic acid

EXAMPLE 7.14

{4-[4-Carbamoyl-5-(3-hexylureido)-1H-imidazol-2-ylmethoxy]phenyl}acetic acid

EXAMPLE 7.15

5-[4-Carbamoyl-5-(3-cyclohexylureido)-1H-imidazol-2-yl]furan-2-carboxylic acid

EXAMPLE 7.16

5-{4-Carbamoyl-5-[3-(2-fluorobenzyl)ureido]-1H-imidazol-2-ylmethyl}furan-2-carboxylic acid

EXAMPLE 7.17

[4-(4-Carbamoyl-5-{3-[2-(2,3-dimethoxyphenyl)ethyl]ureido}-1H-imidazol-2-ylmethoxy)phenyl]acetic acid

EXAMPLE 7.18

5-{4-Carbamoyl-5-[3-(4-trifluoromethylphenyl)ureido]-1H-imidazol-2-yl-methyl}thiophene-2-carboxylic acid

EXAMPLE 8

5-(4-tert-Butylbenzoylamino)-2-(5-cyclopropylcarbamoylfuran-2-ylmethyl)-1H-imidazole-4-carboxamide To a solution of 150 mg (0.36 mM) of {4-[4-carbamoyl-5-(4-tert-butyl-benzoylamino)-1H-imidazol-2-yl] phenoxy}acetic acid in 1.5 ml of DMF are added 22.9 mg (0.40 M) of cyclopropylamine and 210 mg (0.40 mM) of PyBOP.

Finally, 0.2 ml (1.18 mmol) of N-ethyldiisopropylamine is added. The reaction medium is stirred at 20° C. for 16 hours. Demineralized water is then added and the mixture is extracted with ethyl acetate. The organic phase is washed with demineralized water, dried over sodium sulfate and concentrated under vacuum to give an oil, which crystallizes from diisopropyl ether. The solid is filtered off and washed with diisopropyl ether to give 108.3 mg of 5-(4-tert-butylbenzoylamino)-2-(5-cyclopropylcarbamoylfuran-2-ylmethyl)-1H-imidazole-4-carboxamide.

Yield: 66%.

$^1$H NMR (200 MHz/DMSO-d6) δ (ppm): 0.36 (m, 2H); 0.48 (m, 2H); 1.12 (s, 9H); 2.54 (m, 1H); 3.97 (s, 2H); 6.13 (d, 1H); 6.82 (d, 1H); 7.15 (d, 2H); 7.43 (2H, d); 7.65 (d, 2H); 8.06 (s, 1H); 11.01 (s, 1H); 12.64 (s, 1H).

By way of example, the compounds below are prepared, optionally with minor modifications, according to the procedure described in Example 8:

EXAMPLE 8.2

2-(4-Diethylcarbamoylmethoxyphenyl)-5-(4-pentylbenzoylamino)-1H-imidazole-4-carboxamide Empirical formula: $C_{28}H_{35}N_5O_4$=505.61;
Mass spectrum: 504.5 (M−).

EXAMPLE 8.3

2-[5-(Morpholine-4-carbonyl)furan-2-ylmethyl]-5-(4-propylbenzoylamino)-1H-imidazole-4-carboxamide Empirical formula: $C_{24}H_{27}N_5O_5$=465.5;
Mass spectrum: 464.1 (M−).

EXAMPLE 8.4

5-(4-Propylbenzoylamino)-2-[5-(pyrrolidine-1-carbonyl)furan-2-ylmethyl]-1H-imidazole-4-carboxamide Empirical formula: $C_{24}H_{27}N_5O_4$=449.5;
Mass spectrum: 448.1 (M−).

EXAMPLE 8.5

5-(4-tert-Butylbenzoylamino)-2-[5-(pyrrolidine-1-carbonyl)furan-2-yl-methyl]-1H-imidazole-4-carboxamide Empirical formula: $C_{23}H_{29}N_5O_4$=463.53;
Mass spectrum: 462.2 (M−).

EXAMPLE 8.6

5-[3-(4-Butylphenyl)ureido]-2-[5-(piperidine-1-carbonyl)furan-2-ylmethyl]-1H-imidazole-4-carboxamide Empirical formula: $C_{26}H_{32}N_6O_4$=492.57;
Mass spectrum: 493.1 (M+).

EXAMPLE 8.7
2-[4-(2-Morpholin-4-yl-2-oxoethoxy)phenyl]-5-(4-pentylbenzoylamino)-1H-imidazole-4-carboxamide

EXAMPLE 8.8
2-(5-Isobutylcarbamoylfuran-2-ylmethyl)-5-(4-propyl benzoylamino)-1H-imidazole-4-carboxamide

EXAMPLE 8.9
2-(5-Diethylcarbamoylfuran-2-ylmethyl)-5-(4-propylbenzoylamino)-1H-imidazole-4-carboxamide

EXAMPLE 8.10
5-[3-(4-Butylphenyl)ureido]-2-(5-diethylcarbamoylfuran-2-ylmethyl)-1H-imidazole-4-carboxamide

EXAMPLES OF BIOLOGICAL ACTIVITY

Method for Measuring the Inhibition of Human Liver Recombinant Fructose-1,6-bisphosphatase The enzymatic activity is measured by using a spectrophotometric method by means of reactions coupling the formation of the product (fructose-6-phosphate) to the reduction of NADP+ via phosphoglucoisomerase (PGI) and glucose-6-phosphate dehydrogenase (G6PDH).

The reaction mixtures (250 µl) are prepared in 96-well plates and are composed of 20 mM triethanolamine, pH 7.5, 2 mM $MgCl_2$, 0.1 mM EDTA, 40 mM ammonium sulfate, 0.5 mM NADP, 1 U/ml G6PDH, 1 U/ml PGI and 0.167 mM of substrate (fructose-1,6-bisphosphate).

The inhibitors are prepared at $10^{-2}$ M in 100% DMSO and tested at $10^{-5}$ M (DMSO 0.1% final).

The reactions are initiated by addition of human liver recombinant enzyme fructose-1,6-bisphosphatase (hFBPase) and monitored for 30 minutes at 340 nm, at room temperature, in a Tecan plate reader.

Inhibition of Human Liver Recombinant Fructose-1,6-Bisphosphatase

| Example | Structure | $IC_{50}$ (µM) (hFBPase) |
|---|---|---|
| 6.8 | 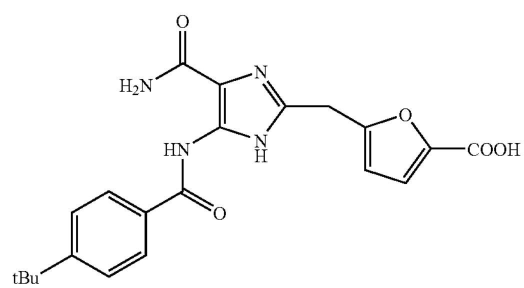 [SMILES: CC(C)(C)c1ccc(C(=O)Nc2[nH]c(Cc3ccc(C(=O)O)o3)nc2C(N)=O)cc1] | 23 |
| 6 | 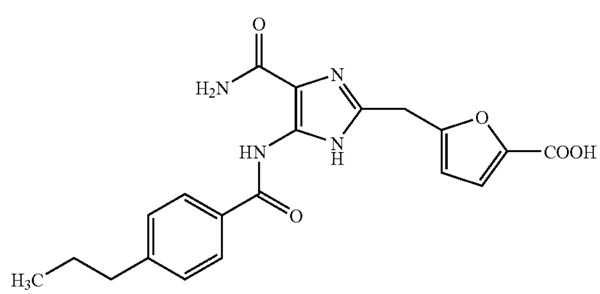 | 28 |
| 7.8 | 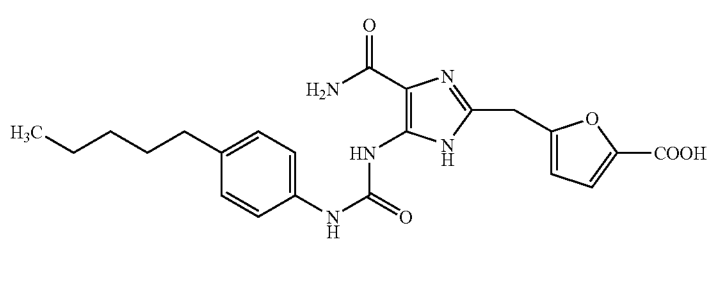 [SMILES: CCCCCc1ccc(NC(=O)Nc2[nH]c(Cc3ccc(C(=O)O)o3)nc2C(N)=O)cc1] | 24 |

| Example | Structure | IC$_{50}$ (μM) (hFBPase) |
|---|---|---|
| 8.5 | 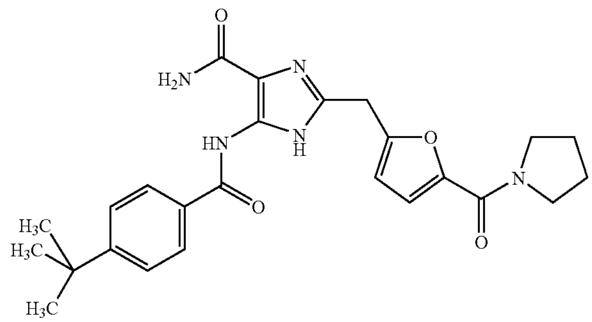 [SMILES: CC(C)(C)c1ccc(C(=O)Nc2[nH]c(Cc3ccc(C(=O)N4CCCC4)o3)nc2C(N)=O)cc1] | 36 |
| 6.9 | 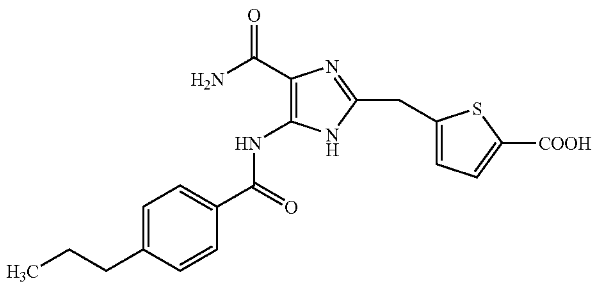 [SMILES: CCCc1ccc(C(=O)Nc2[nH]c(Cc3ccc(C(=O)O)s3)nc2C(N)=O)cc1] | 36 |
| 7.9 | 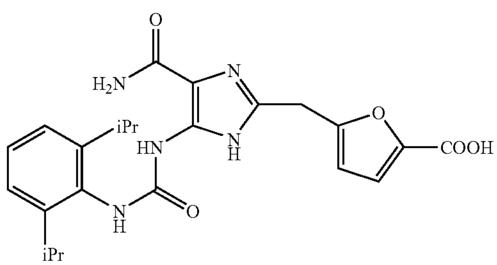 [SMILES: CC(C)c1cccc(C(C)C)c1NC(=O)Nc1[nH]c(Cc2ccc(C(=O)O)o2)nc1C(N)=O] | 42 |

The invention claimed is:

1. A compound of the formula (I):

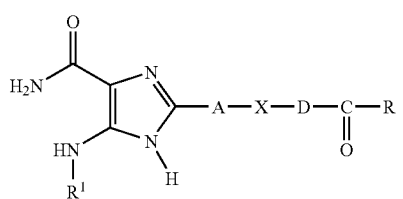

in which
R represents a group chosen from: —OH, —OR$^e$ and —NR$^a$R$^b$; and
R$^a$ and R$^b$, which may be identical or different, are independently chosen from a hydrogen atom and a radical Z, or alternatively may form, together with the nitrogen atom that bears them, a saturated or unsaturated 5- or 6-membered ring optionally containing from 1 to 3 heteroatoms, the said ring optionally being substituted by 1 to 3 groups chosen from Y; and
R$^e$ represents a (C$_1$-C$_8$)alkyl radical, optionally substituted by one or more groups independently chosen from halogen, (C$_1$-C$_8$)alkyl, (C$_1$-C$_8$)alkoxy, (C$_3$-C$_8$)cycloalkyl and (C$_6$-C$_{14}$)aryl; and R$^1$ represents one of the following groups:

and
R$^2$ represents a substituted or unsubstituted aryl radical; and
-A-X-D- represents a group in which, independently between A, X and D:
A represents a divalent group obtained after abstraction of a hydrogen atom from a (C$_1$-C$_{20}$)alkyl, optionally substituted by one or more groups chosen from Y; and
D represents a bond; and
X represents a divalent group obtained after abstraction of a hydrogen atom from a monovalent radical chosen from:
  (C$_6$-C$_{14}$) aryl, which may itself be optionally substituted by one or more groups chosen from Y;
  (C$_5$-C$_{14}$)heteroaryl, which may itself be optionally substituted by one or more groups chosen from Y, this heteroaryl group comprising one or more heteroatoms chosen from N, O and S;
  (C$_3$-C$_8$)cycloalkyl, which may itself be optionally substituted by one or more groups chosen from Y;

(C$_4$-C$_8$)cycloalkenyl, which may itself be optionally substituted by one or more groups chosen from Y; and (C$_3$-C$_8$)heterocycloalkyl, which may itself be optionally substituted by one or more groups chosen from Y, this heterocycloalkyl group comprising one or more heteroatoms chosen from N, O and S; and Y represents a radical chosen from hydroxyl, thio, halogen, cyano, trifluoromethoxy, trifluoromethyl, carboxyl, carboxymethyl or carboxyethyl, (C$_1$-C$_8$)alkyl, (C$_1$-C$_8$)alkoxy, (C$_1$-C$_8$)alkylamino, (C$_6$-C$_{14}$)aryl, (C$_6$-C$_{14}$)aryloxy, (C$_6$-C$_{14}$)aryl(C$_1$-C$_8$)alkoxy, amino, oxo and carbamoyl; and Z represents a group chosen from:
(C$_1$-C$_{20}$)alkyl optionally substituted by one or more groups chosen from Y;
(C$_2$-C$_{20}$)alkenyl, optionally substituted by one or more groups chosen from Y;
(C$_6$-C$_{14}$)aryl or (C$_6$-C$_{14}$)aryl(C$_1$-C$_{20}$)alkyl, the aryl group of each of these groups itself optionally being substituted by one or more groups chosen from Y; and
(C$_6$-C$_{14}$)heteroaryl or (C$_6$-C$_{14}$)heteroaryl(C$_1$-C$_{20}$)alkyl, the heteroaryl group of each of these groups itself optionally being substituted by one or more groups chosen from Y, this heteroaryl group comprising one or more heteroatoms chosen from N, O and S, or
the possible tautomeric forms thereof and the possible enantiomers, diastereoisomers, epimers and organic or mineral salts thereof.

2. A compound according to claim 1, chosen from:
5-[5-(4-tert-butylbenzoylamino)-4-carbamoyl-1H-imidazol-2-ylmethyl]furan-2-carboxylic acid;
5-[4-carbamoyl-5-(4-propylbenzoylamino)-1H-imidazol-2-ylmethyl]furan-2-carboxylic acid;
5-{4-carbamoyl-5-[3-(4-pentylphenyl)ureido]-1H-imidazol-2-ylmethyl}furan-2-carboxylic acid;
5-{4-carbamoyl-5-[3-(2,6-diisopropylphenyl)ureido]-1H-imidazol-2-ylmethyl}furan-2-carboxylic acid;
5-{5-[3-(4-butylphenyl)ureido]-4-carbamoyl-1H-imidazol-2-ylmethyl}furan-2-carboxylic acid;
5-{4-carbamoyl-5-[3-(3-phenoxyphenyl)ureido]-1H-imidazol-2-ylmethyl}furan-2-carboxylic acid;
5-[4-carbamoyl-5-(4-propylbenzoylamino)-1H-imidazol-2-ylmethyl]thiophene-2-carboxylic acid; and
5-(4-tert-butylbenzoylamino)-2-[5-(pyrrolidine-1-carbonyl)furan-2-ylmethyl]-1H-imidazole-4-carboxamide,
or
the possible tautomeric forms thereof and the possible enantiomers, diastereoisomers, epimers and organic or mineral salts thereof.

3. Process for the preparation of a compound as defined in claim 1, characterized in that a compound A2 is prepared according to the scheme:

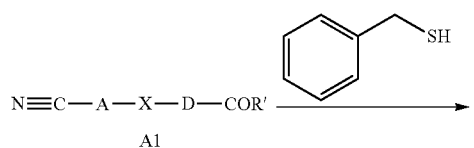

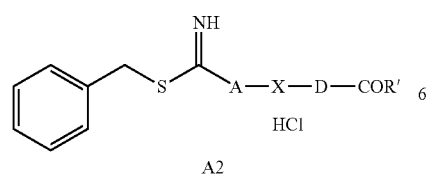

in which A, X and D are as described in claim 1, R' having the same definition as R defined above, with the exception of the hydroxyl radical, via the action of a mercaptan derivative on a nitrile derivative chosen from A1, in which A, X, D and R' are as described above, in a solvent in the presence of hydrochloric acid introduced in gaseous form into the reaction medium, at a temperature ranging from −10° C. to 25° C., for 1 hour to 72 hours, which compound of the formula A2 is converted into a compound of the formula A3 according to the scheme:

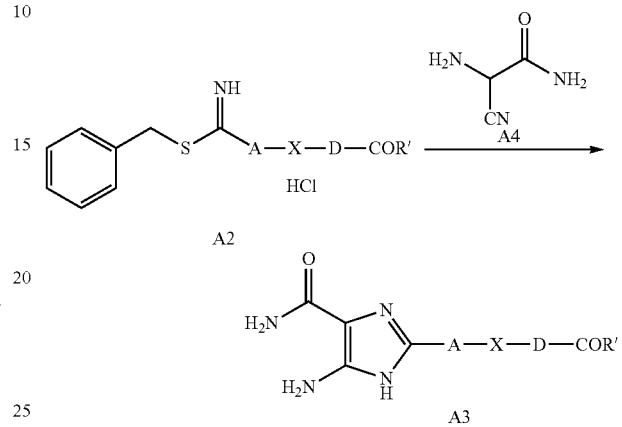

in which A, X, D and R' are as described above, by reacting the thio imino ether A2 with the aminocyanoacetamide A4, in a solvent, in the presence of a base, at a temperature ranging from room temperature to the boiling point of the solvent under consideration, and compound A3 can then be either:

optionally subjected to a deprotection reaction, under standard conditions known to those skilled in the art, according to the following scheme:

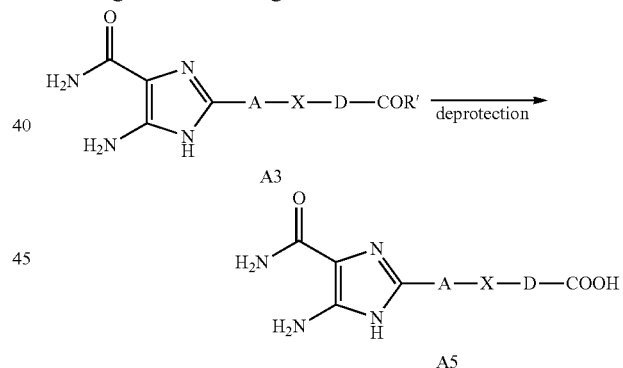

to give compound A5, in which A, D and X are as defined above, the compounds of the formulae A3 and A5 forming the set of compounds of the formula (I) in which R$^1$ represents a hydrogen atom;

or converted into a compound of the formula B1, according to the following scheme:

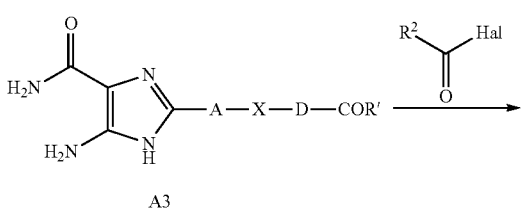

-continued

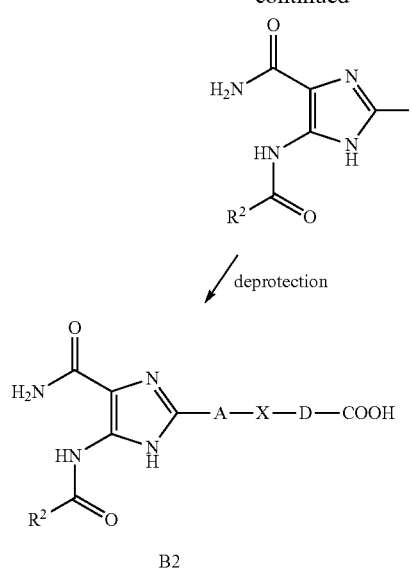

in which A, D, X and R' are as described above and R² is as defined in claim 1, via the action of an acid halide of the formula Hal—CO—R², in which R² is as defined above, in the presence of an organic or mineral base, in a solvent, or alternatively via acid-activation methods, using coupling agents, compound B1 then being optionally deprotected to compound B2 according to known deprotection methods, the compounds of the formulae B1 and B2 forming the set of compounds of the formula (I) in which R¹ represents the group:

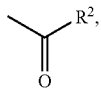

or alternatively converted into a compound of the formula C1, according to the following scheme:

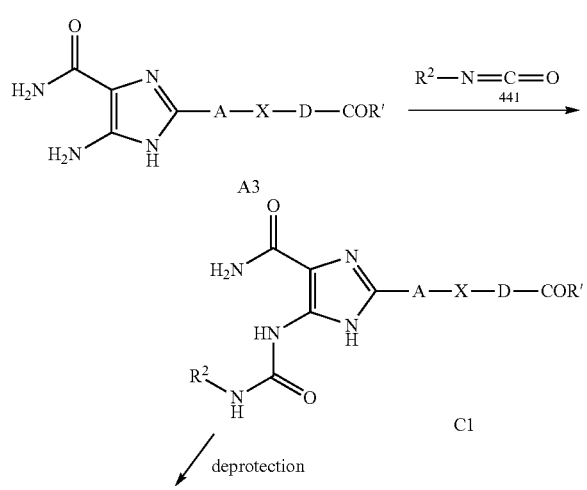

-continued

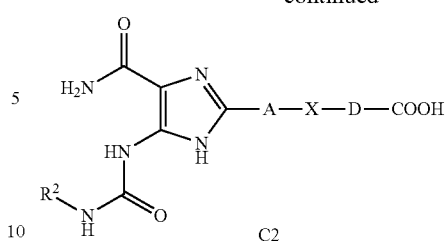

in which A, D, X, R' and R² are as defined above, via the action of the isocyanate of the formula R²—N=C=O, in a solvent, at a temperature ranging from 0° C. to the boiling point of the solvent used, compound C1 then being optionally deprotected to compound C2 according to known deprotection methods the compounds of the formulae C1 and C2 forming the set of compounds of the formula (I) in which R¹ represents the group:

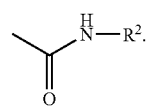

4. Process according to claim 3 for the preparation of the compounds of the general formula (I) and for which R represents the group —NR$^a$R$^b$, starting with compounds B2 and C2 as defined above, according to the following reaction schemes:

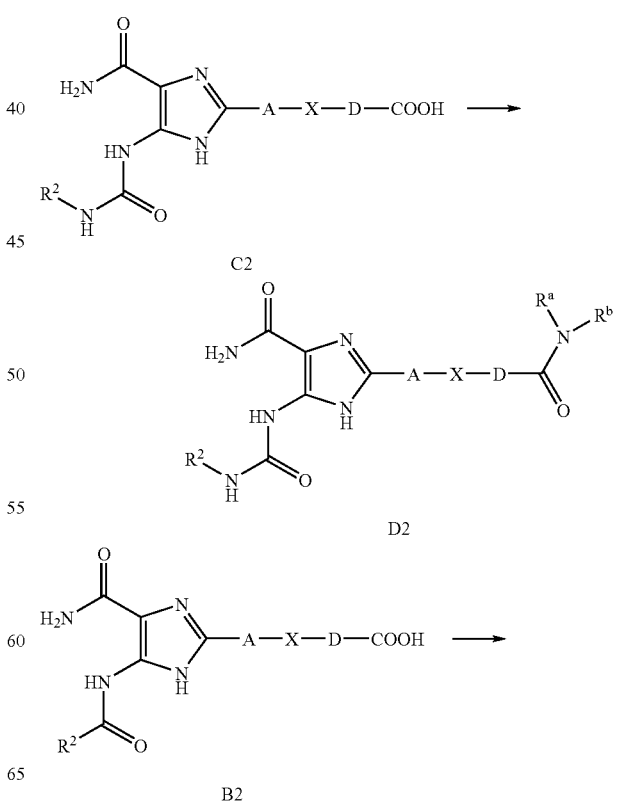

-continued

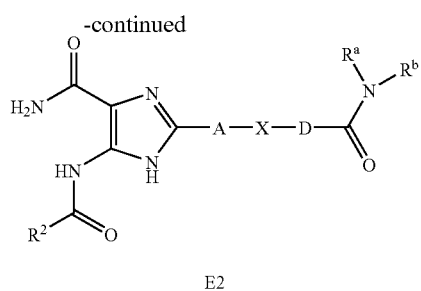

E2 via the action of the acid chloride under consideration with an amine, or using mixed anhydride techniques, or alternatively via the action of coupling agents.

5. Pharmaceutical composition comprising a pharmaceutically effective amount of at least one compound of the formula (I) as defined in claim 1, and one or more pharmaceutically acceptable excipients.

6. A method for treating type II diabetes, dyslipidaemia, obesity, arterial hypertension, atherosclerosis, retinopathy, neuropathy, myocardial ischaemia, hypercholesterolaemia or hyperlipidaemia comprising administering a compound of claim 1 to a patient in order to effect fructose-1,6-bisphosphatase inhibition.

* * * * *

UNITED STATES PATENT AND TRADEMARK OFFICE
CERTIFICATE OF CORRECTION

PATENT NO. : 8,362,057 B2  Page 1 of 1
APPLICATION NO. : 11/997514
DATED : January 29, 2013
INVENTOR(S) : Moinet et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1400 days.

Signed and Sealed this
First Day of September, 2015

Michelle K. Lee
*Director of the United States Patent and Trademark Office*